United States Patent [19]

Leise, Jr. et al.

[11] Patent Number: 5,139,492

[45] Date of Patent: Aug. 18, 1992

[54] TWO-PIECE OSTOMY APPLIANCE WITH SLIDING TRANSVERSE INTERLOCK

[75] Inventors: Walter F. Leise, Jr., Lindenhurst; Michael R. Lavender, Round Lake, both of Ill.

[73] Assignee: Hollister Incorporated, Libertyville, Ill.

[21] Appl. No.: 823,973

[22] Filed: Jan. 22, 1992

[51] Int. Cl.$^5$ .............................. A61F 5/44
[52] U.S. Cl. .......................... 604/339; 604/332
[58] Field of Search ........................ 604/332–345, 604/277, 278

[56] References Cited

U.S. PATENT DOCUMENTS

| | | | |
|---|---|---|---|
| 4,213,458 | 7/1980 | Nolan et al. | 604/344 |
| 4,359,051 | 11/1982 | Oczkowski | 128/283 |
| 4,406,659 | 9/1983 | Broida | 604/339 |
| 4,419,100 | 12/1983 | Alexander | 604/339 |
| 4,610,676 | 9/1986 | Schneider et al. | 604/339 |
| 4,610,677 | 9/1986 | Mohiuddin | 604/339 |

FOREIGN PATENT DOCUMENTS 1370622  10/1974  United Kingdom ................ 604/339

Primary Examiner—Randall L. Green
Assistant Examiner—R. Clarke
Attorney, Agent, or Firm—Tilton, Fallon, Lungmus

[57] ABSTRACT

A two-piece ostomy appliance with a low profile coupling ring assembly in which the rings are moved transversely rather than axially into and out of interlocked condition. The faceplate ring has an upturned flange along its lower border and the pouch ring has a downturned flange along its upper border, with the flange of each ring defining a channel for receiving a peripheral portion of the other ring for locking the rings together as they are shifted transversely (radially) into axial alignment. The configuration of each ring about the stoma opening thereof results in a preloaded annular seal when the rings are coupled together.

8 Claims, 1 Drawing Sheet

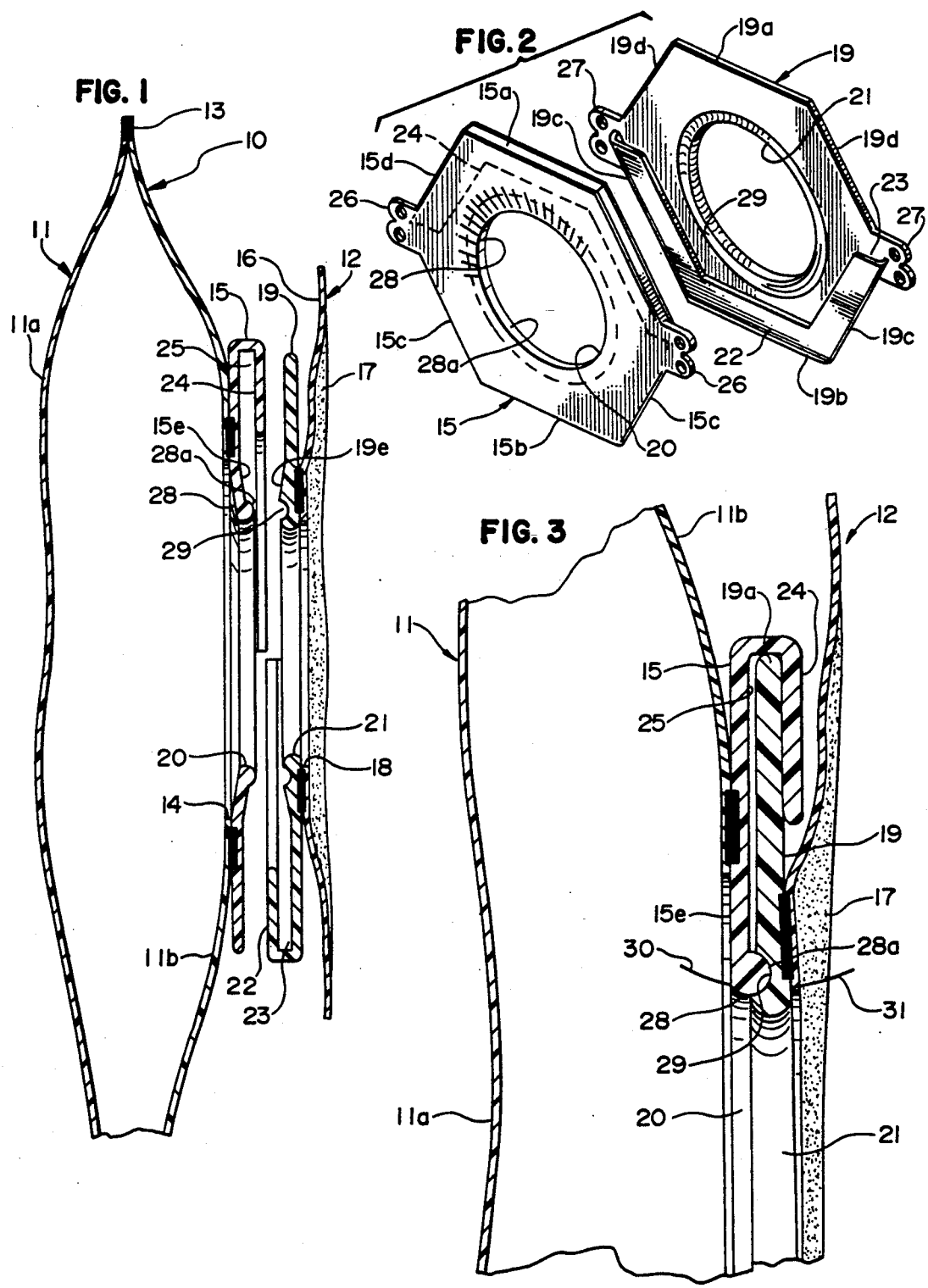

TWO-PIECE OSTOMY APPLIANCE WITH SLIDING TRANSVERSE INTERLOCK

BACKGROUND AND SUMMARY

Two-piece ostomy appliances commonly consist of a collection pouch and an adhesive faceplate that are equipped with flexible plastic coupling rings which latch together and which permit a wearer to detach and replace the pouch component without removing the adhesive faceplate component from his/her body. The latching/unlatching actions typically involve limited flexing of one or both rings as they are urged together or pulled apart in axial directions in much the same manner as the lids of conventional plastic containers are closed and opened. However, in the case of an ostomy appliance, the wearer may be required to apply inward pressure to the sensitive peristomal area to latch the rings axially together and, conversely, to apply a pulling force to the same peristomal area when the rings are separated.

Although conventional ostomy coupling rings are joined or separated in axial directions, the sealing and/or latching forces are usually radially directed to maintain the surfaces of the parts in tight circumferential engagement. Mating the rings together is often difficult for users and generally requires a two-handed operation. That is because the procedure of joining the rings together normally involves initiating attachment at one point and then progressing in opposite circumferential directions until the rings have been squeezed together about their full circumferences. Since engagement progresses along two paths at the same time, the use of two hands is usually required. Furthermore, in such a system even initiating engagement may be difficult because the rings often have a tendency to slip out of alignment and obstruct circumferential progression of the coupling action.

With conventional coupling ring arrangements, there is often the further concern that the parts might become unintentionally detached, since all that would be required for such detachment is the occurrence of an axial pulling force of sufficient magnitude. Efforts to reduce the possibilities of unintended detachment have commonly involved increasing the stiffness of the rings or the extent of ring deformation when coupled, both of which also tend to make intentional attachment and detachment even more difficult for the wearer. That in turn increases the possibilities that a wearer, especially one who is elderly, infirm, or lacking in strength and dexterity, might conclude that complete coupling has been effected when in fact the rings have been only partially or imperfectly joined.

Conventional coupling ring arrangements have an additional shortcoming in that their interfacing surfaces are circular and may therefore permit rotational movement of a pouch ring with respect to a faceplate ring when the parts are fully coupled. Such rotation may result in a gradual "working off" of a pouch ring from a faceplate ring during physical activity or even when a patient rolls or turns about during sleep.

Accordingly, a main aspect of this invention lies in providing a two-piece ostomy appliance with coupling rings that do not require axially-directed movements for latching and unlatching and which provide full security against accidental detachment even when substantial axially-directed forces are exerted. Despite such high resistance to inadvertent detachment, the rings require only minimal force for intentional connection or separation, thereby eliminating or at least greatly reducing the manipulative problems often encountered by ostomates in attaching and removing prior two-piece appliances.

Unlike conventional coupling ring assemblies, the assembly of this invention locks the parts against independent relative rotation, thereby avoiding the possibility that rotational forces applied to a pouch might result in unintended separation. A further aspect of the invention lies in providing an assembly in which a fluid-tight preloaded seal is produced by axial flexion of one or both parts as they are urged transversely together into fully latched or interlocked condition.

Briefly, the appliance comprises a collection pouch and an adhesive faceplate equipped with relatively stiff but flexible plastic coupling rings for detachably securing the components together. The faceplate coupling ring has an upwardly-turned flange along a lower side thereof facing away from the faceplate to define an upwardly-directed first channel for slidably receiving a lower peripheral portion of the pouch coupling ring and, conversely, the pouch coupling ring has a downwardly-turned flange along its upper side facing away from the pouch to define a downwardly-directed channel for slidably receiving the upper peripheral portion of the faceplate coupling ring. Consequently, when the rings are urged transversely together, the channel of each respective ring receives a peripheral portion of the opposing ring to lock the rings against axial separation.

Most advantageously, the rings are polygonal in outline so that, when mated together, they are locked against relative rotation. A hexagonal shape is particularly effective because it also facilitates alignment of the coupling rings as they are urged together.

A fluid-tight seal is formed by mating engagement between inner rim portions of the respective rings located immediately adjacent the stoma openings of those rings. At least one, and preferably both, of the inner rim portions is axially offset to provide an axial preload for forceably maintaining the inner rim portions in fluid-tight engagement when the rings are coupled together. As the rings are urged transversely into alignment during a coupling operation, the inner rim portions are cammed into tensioned conditions and, when fully aligned, snap into sealing engagement to provide an audible and tactile indication that full coupling has occurred.

Other features, advantages, and objects of the invention will become apparent from the specification and drawings.

DRAWINGS

FIG. 1 is a vertical sectional view of a two-piece ostomy appliance embodying the present invention, the coupling rings of the appliance being shown in disconnected condition.

FIG. 2 is a perspective view of the coupling rings in disconnected condition.

FIG. 3 is an enlarged fragmentary sectional view similiar to FIG. 1 but showing the rings in connected condition.

DETAILED DESCRIPTION OF PREFERRED EMBODIMENT

Referring to the drawings, the numeral 10 generally designates a two-piece ostomy appliance comprising a pouch (or pouch subassembly) 11 and a faceplate (or faceplate subassembly) 12. The pouch has a pair of walls 11a, 11b formed of thin, flexible, thermoplastic material peripherally joined together by heat seal 13. Wall 11b has a stoma-receiving opening 14, and a coupling ring or member 15 is secured to the outer surface of wall 11b immediately about that opening.

Faceplate 12 includes a thin, flexible patch or wafer 16 having a pressure-sensitive adhesive coating 17 along its body-facing surface. Like pouch 11, patch 16 may be formed of fluid-impervious non-porous thermoplastic film. Alternatively, the patch may be made of flexible microporous sheet material of any of various types well known in the medical field. Also, as known in the art, the body-facing surface of the patch may have a ring of a hydrocolloid-containing skin barrier material secured thereto to provide a moisture absorbing adhesive seal against the wearer's body. Reference may be had to co-owned patent Nos. 4,213,458, 4,419,100, 4,610,676, and 4,610,677 for further details concerning such features of faceplate construction.

Patch 16 has a stoma-receiving opening 18 that is concentric with opening 14 of the pouch when the faceplate and pouch are assembled. A faceplate coupling ring or member 19 is heat sealed or otherwise permanently secured to the pouch-facing surface of patch 16 about opening 18, as shown most clearly in FIG. 1.

In FIG. 2, coupling rings 15 and 19 are shown separately and in spaced condition for clarity of illustration. Each ring is molded from a tough, durable, and flexible polymeric material with appreciable elastic recovery such as, for example, polyethylene or polypropylene. The term "ring" is used herein because the members 15 and 19 are generally annular with enlarged central openings 20 and 21, respectively, of generally circular shape. The outer edges of the rings may also be circular in outline; however, in the preferred embodiment depicted in the drawings, such margins are polygonal. Ideally, each ring is hexagonal with ring 15 having upper and lower parallel edges 15a and 15b that are disposed generally horizontally when the appliance is worn, a pair of lateral edges 15c sloping upwardly and outwardly from the ends of lower edge 15b, and a second pair of lateral edges 15d sloping downwardly and outwardly from the ends of upper edge 15a. Ring 19 has corresponding horizontal upper and lower edges 19a and 19b, a pair of upwardly and outwardly sloping lateral edges 19c, and a pair of downwardly and outwardly sloping lateral edges 19d. Along the lower portion of faceplate coupling ring 19, on that side of that ring facing away from adhesive patch 16, is an upwardly turned flange 22 defining an upwardly and inwardly facing channel 23 for slidably receiving the lower peripheral portion of the pouch ring 15, that extends along edges 15b and 15c.

The pouch coupling ring 15 is also provided with a flange 24 along edges 15a and 15b that defines a downwardly and inwardly facing channel 25 on that side of the ring opposite from pouch 11. Channel 25 is dimensioned for slidably receiving the upper peripheral portion of faceplate ring 19, that is, the portion extending along edges 19a and 19b.

It is believed apparent that to assemble the coupling rings, pouch ring 15 is simply lowered so that the upper peripheral portion of the faceplate ring is received in channel 25 and the lower peripheral portion of the pouch ring is received in channel 23. The width of each channel, measured axially with respect to each ring, is only slightly greater than the thickness of the ring portion slidably receivable therein, as depicted in FIG. 3. As a result, the parts may be easily fitted together by transverse or radial sliding movement but, when so fitted, are securely and positively interlocked against axial separation.

Since the rings are of corresponding polygonal shape, they automatically interlock to prevent or resist independent rotation when they are fully mated with their openings 20 and 21 in coaxial alignment as depicted in FIG. 3. While it is believed desirable to prevent relative rotation of the coupling rings for purposes of overcoming or reducing problems of unintended detachment previously described, it is to be understood that rings 15 and 19 might if desired have peripheral edges of circular shape concentric with openings 20 and 21, and with flanges 22 and 24 defining arcuate channels, in which case other means would be required to prevent or reduce relative rotation of the parts. One such means is depicted in FIG. 2 and takes the form of pairs of apertured ears 26 and 27 that project laterally from the rings to provide attachment means for a retention belt that if used would supplement the inherent anti-rotational effects of the polygonal (hexagonal) ring construction shown and would also prevent relative rotation of such rings even if their peripheral edges and channels were instead circular or arcuate in shape.

The structure so far described is responsible for providing a positive interlock capable of resisting axial forces of separation that might be encountered in use of the appliance while, at the same time, providing a system in which intentional coupling and uncoupling may be easily accomplished by simply lowering and raising the pouch ring 15 with respect to the faceplate ring 19. Aside from the interlock, however, the formation of a liquid-tight seal between the parts results from mating engagement and axial compressive forces generated between inner rim portions 15e and 19e immediately surrounding openings 20 and 21, of the two rings. Referring to FIG. 1, it will be observed that inner rim portion 15e of pouch coupling ring 15 is slightly frusto-conical in shape, sloping inwardly and axially in a direction away from pouch 11 and towards faceplate coupling ring 19. A rib or bead 28 is provided along the inner limits of rim portion 15e and defines a smoothly-rounded annular surface 28a for engaging the inner rim portion 19e of faceplate ring 19.

Similarly, the inner rim 19e of the faceplate ring may have a frusto-conical surface that slopes inwardly and axially towards pouch ring 15. Rim portion 19e is provided with an annular groove 29 that is dimensioned to receive the smoothly-rounded surface 28a of rib 28. While both of the inner rim portions 15e and 19e are shown to have frusto-conical surfaces, it is to be understood that only one such portion may be so configured, the primary requirement being that when the rings are coupled as shown in FIG. 3, at least one of the rim portions is under axial tension, having been cammed axially out of its untensioned position as the rings were shifted transversely together into their fully coupled condition. Axial preload forces are therefore exerted in the directions indicated by arrows 30 and 31 to maintain rib 20 in tight sealing engagement in groove 29. The preload also tends to urge the outer peripheral portion of each ring against that surface of each flange 22 and 24 facing channel 23 and 25, respectively, thereby contributing in maintaining the rings in latched condition until such time as separation is desired.

It is believed apparent that as rings 15 and 19 are urged transversely together, the inner rim portions 15e and 19e will be cammed in opposite directions away from each other until coaxial alignment has been achieved, at which time rib 28a snaps into groove 29 to produce a forceful, fluid-tight seal. Since the camming action places both rings under tension, the final mating of the parts, when rib 28a is received in groove 29, generates a signal that may be both audibly and tactily received, thereby informing the user that the parts are fully coupled together.

While an embodiment of the invention has been described in considerable detail for purposes of illustration, it will be understood by those skilled in the art that many of such details may be varied without departing from the spirit and scope of the invention.

We claim:

1. A two-piece ostomy appliance comprising a collection pouch and an adhesive faceplate respectively provided with coupling rings for detachably securing said pouch and faceplate together; said rings being formed of relatively stiff but flexible polymeric material each having a generally centrally-disposed stoma opening therethrough positioned and arranged to align with each other when said rings are coupled together; said faceplate coupling ring having an upwardly-turned flange means along a lower side thereof facing away from said faceplate to define an upwardly-directed first channel for slidably receiving a lower peripheral portion of said pouch coupling ring; and said pouch coupling ring having downwardly-turned flange means along an upper side thereof facing away from said pouch to define a downwardly-directed channel for slidably receiving an upper peripheral portion of said faceplate coupling ring; whereby, when said rings are urged transversely together, said first and second channels receive said lower and upper peripheral portions, respectively, of said pouch and faceplate coupling rings to lock said rings against axial separation.

2. The appliance of claim 1 in which said coupling rings are polygonal in outline.

3. The appliance of claim 2 in which at least one of said peripheral portions includes a generally horizontal edge portion and a pair of sloping lateral edge portions at each end of said horizontal edge portion; and said channel receiving the same includes a horizontal portion and a pair of sloping lateral portions matable with said horizontal and lateral edge portions of said peripheral portion receivable in said channel.

4. The appliance of claim 3 in which each of said coupling rings is generally hexagonal in outline.

5. The appliance of claims 1, 2, or 3 in which said stoma openings are located in inner rim portions of said coupling rings; said inner rim portion of one of said rings having an annular groove extending about said stoma opening along that side of said one ring facing the other of said rings; and said inner rim portion of the other of said rings having an annular rib sealingly received in said groove when said rings are coupled together.

6. The appliance of claim 5 in which said inner rim portion of at least one of said rings is axially offset when said one ring is untensioned to provide a preload for tightly maintaining said rib in said groove when said rings are coupled together.

7. The appliance of claim 6 in which the inner rim portions of both of said rings are axially offset for preloading the seal between said rings when they are coupled together.

8. The appliance of claim 1 in which each of said rings includes a pair of apertured lateral projections for attachment of a retention belt.

* * * * *